United States Patent [19]

Mao

[11] Patent Number: 5,133,718
[45] Date of Patent: Jul. 28, 1992

[54] Z-SHAPED BONEPLATE AND THE METHOD FOR INTERNAL FIXATION OF LONG BONE FRACTURES AND ALLOGRAFT MATERIALS

[76] Inventor: Zhang Mao, 185 Edmonton Dr., Willowdale, Toronto, Canada, M2J 3X4

[21] Appl. No.: 500,589

[22] Filed: Mar. 28, 1990

[30] Foreign Application Priority Data

Apr. 30, 1989 [CN] China .................. 89102645.2

[51] Int. Cl.$^5$ ............................................. A61B 17/58
[52] U.S. Cl. ........................................ 606/69; 606/60
[58] Field of Search .................. 606/60, 62, 69–71, 606/72

[56] References Cited
U.S. PATENT DOCUMENTS 2,133,859 10/1938 Hawley .................................. 606/69
3,955,567 5/1976 Richmond et al. ................... 606/69

Primary Examiner—Robert A. Hafer
Assistant Examiner—Kevin G. Rooney

[57] ABSTRACT

The present invention provides a kind of boneplate for fixation of long bone fracture and allograft materials in humans and mammals. It is a Z-shaped boneplate, which fixes the fractured bone internally by inserting the boneplate into the boneslot. A Z-shaped boneplate is made up of an upper flange member and a lower flange member and both related to a web member. Its cross section is a Z-section beam. The surgical procedure concerning this invention mainly involves cutting a proper boneslot and inserting the boneplate into the boneslot, thus making the upper and lower flanges abut the inner and outer cortexes respectively and avoid bending and torsion between the fractured ends and any displacement between the cross sections of the fractured ends, therefore, provide stable locking of the fractured ends.

7 Claims, 2 Drawing Sheets

Z-SHAPED BONEPLATE AND THE METHOD FOR INTERNAL FIXATION OF LONG BONE FRACTURES AND ALLOGRAFT MATERIALS

BACKGROUND OF THE INVENTION

1. Field of the Invention

This invention relates to a new internal fixation boneplate for long bone fracture, which is characterized by its Z-shaped cross section.

2. Prior Art

The currently used methods for internal fixation of long bone fractures are mainly the following:

(1) Fixation of transplanted massive cortical bone with screws.

(2) Internal fixation with intramedullary nails. This is presently the most commonly used clinical method.

(3) Penetrating fixation with screws.

(4) Fixation with screw plate.

(5) Fixation with compression plate and screws.

The common drawbacks of the above 1 to 4 methods are: long period of postoperation extra immobilization with plaster; unreliability in fixation of a fractured bone; lengthening of the recovery period; arrest of bone growth and development caused by screws; frequent occurrence of bending or broken of the plate and screws which leads to failure of the operation, and having another operation to pull out the screws is very complicated and increases the patient's pain.

Method 5 is a new method which has been popularized during the past 20 years. According to the principle that the closely contacted compression stress between the fractured sections will speed up the recovery, fixing the plate with screws enables the fractured ends to press closely to each other along the bone axis so that the healing period is shortened with no requirement for postoperation extra immobilization. The patient can move a little such as sitting up, turning the body over, etc. One shortcoming of this method is that the big boneplate brings great stimulation to the tissue and should be taken out through a second operation and hence high expense is needed. The major shortcoming of this method is that due to its firm fixation, it is the plate, rather than the bone tissue that the plate fixes, that bears the whole stress conducted from the load limb bears. This hinders the remodeling of the bone construction according to the conduction of its physiological stress during the healing period and causes bone atrophy. As a result, fracture may occur at the end of the plate where normal bone and cancellated bone meet, and refracture may also occur after the plate is removed. These are the bad effects caused by the blindness of increasing the plate bearing load. The present invention overcomes all the above mentioned shortcomings with its specific advantages.

PRESENT INVENTION

Summary of the Present Invention

The present invention provides boneplate for internal fixation which is characterized by its Z-shaped cross section. Longitudinally it is a uniform beam except for those with a tail flange member or with holes in the web member. A Z-shaped boneplate consists of an upper flange member, a lower flange member and a web member. Its fixation is accomplished by the following steps: Cutting a straight slot spanning the fractured ends along the anterior-medial sagittal section direction on the bone surface with the width the same as the thickness of the Z-shaped boneplate; inserting the plate into the slot so that it spans the two sides of the fractured bone with half plate in each end and the fractured bone is then in reduced and aligned condition, with the upper and lower flanges locking the outer and inner surfaces of the bone cortexes respectively and the fractured ends are firmly fixed, any bending, torsion or transverse displacements of the fractured ends are impossible. The traditional method with screws and/or nails is avoided. The material is alloy steel or other kinds of strengthened materials used for orthopedic internal fixation devices.

DESCRIPTION IN DETAIL WITH THE DRAWINGS

Figure 1A:
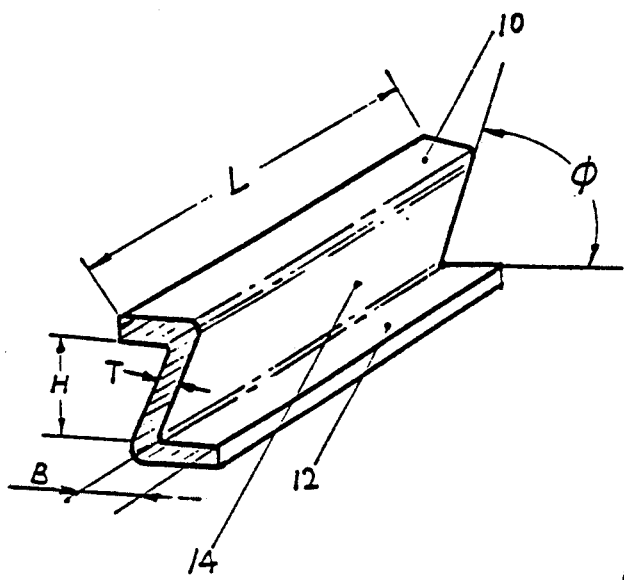
FIG. 1a shows the three-dimensional perspective of the most basic type of Z-shaped boneplate, a Z-section beam with no tail flange member.
Figure 1B:
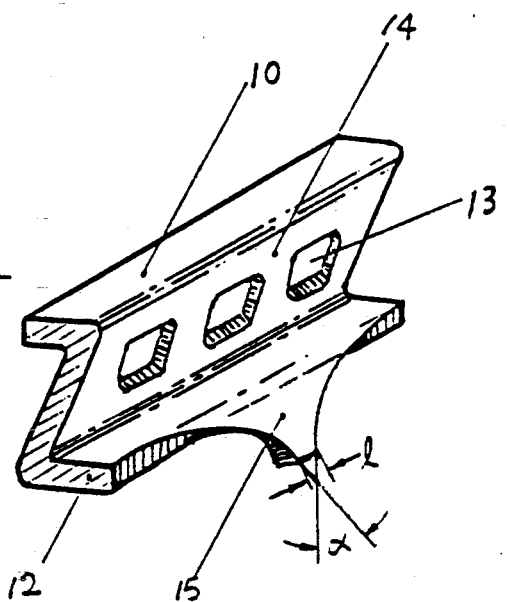
FIG. 1b shows the three-dimensional perspective of a Z-shaped boneplate with tail flange member and holes in the web member.

Following is the detailed description of the present invention in combination with attached drawings:

FIG. 1a-1b shows the three-dimensional perspective of the two basic types of Z-shaped boneplates. They both consist of a web member 14, an upper flange member 10 and a lower flange member 12 which is parallel to the upper flange. FIG. 1a is the most basic type of Z-shaped boneplate with no tail flange member, which is a Z-section beam. Marked out in the drawing are five basic parameters L,H,B,T and $\phi$ which decide the shape and size of a Z-shaped boneplate.

FIG. 1b is a Z-shaped boneplate with a tail flange member 15. Marked in the drawing are the tail flange angle $\alpha$ and the width of the tail l which decides the shape and size of a tail flange member. In the case of $\alpha = 180°$ and $l = 0$, it is a Z-shaped boneplate with no tail flange member as in FIG. 1a. In the drawing, 13 indicates the holes opened on the web member. These holes enables the bone tissue to heal passing through the boneplate, which speeds up the healing and reinforce the fixation.

Figures 2A, 2B, 2C, 2D:
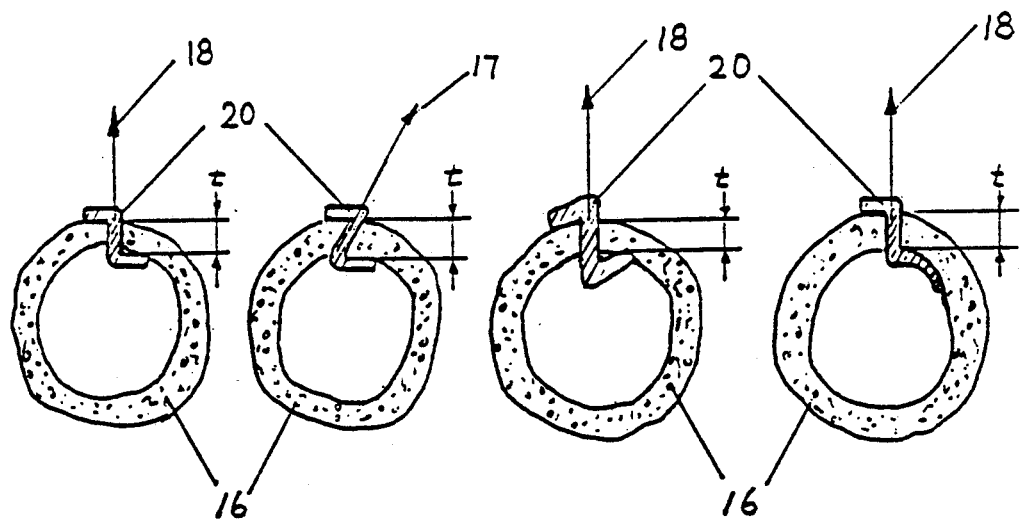
FIG. 2a-2d shows the cross section of fractured ends when using different Z-shaped boneplate for fixation.

FIG. 2 shows the cross section on fractured ends when using a Z-shaped boneplate for fixation. FIG. 2a, 2b and 2c shows the use of Z-shaped boneplate with no tail flange member, and in FIG. 2d with a tail flange member. t indicates the thickness of the bone cortex of the fractured section 16 indicates a long bone and 20 indicates a Z-shaped boneplate. In FIG. 2a and 2d, $\phi = 90°$. In FIG. 2b and 2c, $\phi < 90°$. The above four situations of Z-shaped boneplate fixation involve different directions the web member are inserted. Arrow 18 shows the web member inserted in a centripetal direction. Arrow 17 shows the web member inserted in a non-centripetal direction and the bone slot, too, is in a non-centripetal direction.

Figure 3:
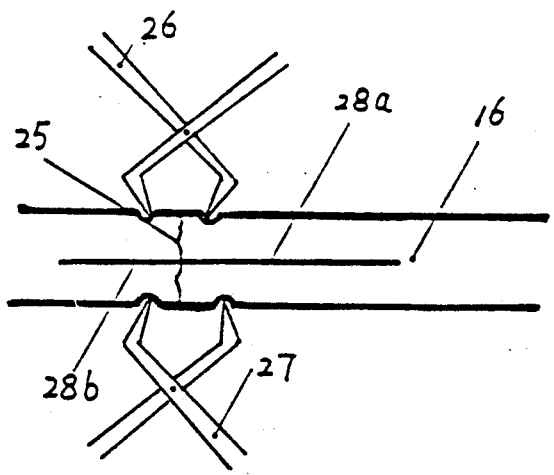
FIG. 3 illustrates the way of reduction for fractured bones.

FIG. 3 shows a fractured long bone 16 and its fractured line 25. The fractured ends are in reduced condition. Use fixing pliers 26 and 27 to clamp the two fractured ends and fix them firmly. Score a straight line 28 along the anterior-medial sagittal section direction on the bone surface with the tip of a knife, with the longer end 28a the same length as the Z-shaped plate, and shorter end 28b, half the length of the Z-shaped boneplate. The straight line is for sawing the boneslot.

Figure 4:
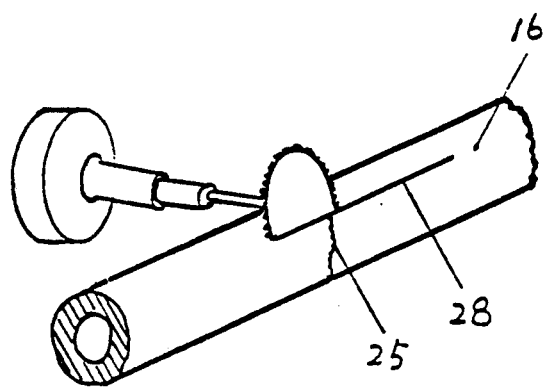
FIG. 4 shows the method of cutting the bone slot.

FIG. 4, Cut a boneslot 28 along the boneslot line marked in FIG. 3 with a boneslot saw, let the breadth of the slot the same as the thickness of the boneplate. The boneslot should be straight, and the direction in extends to the marrow cavity should be the same as the inserting of the web member so that the Z-shaped boneplate can be easily inserted into the slot without being too tight or too loose.

Figure 5:
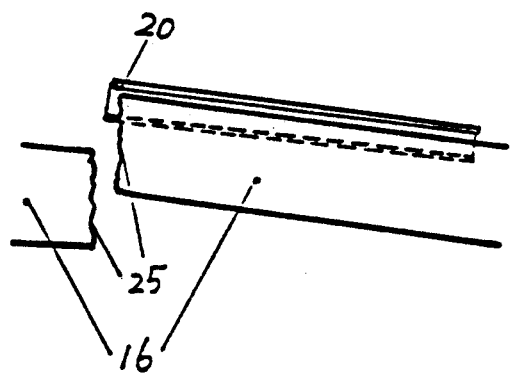
FIG. 5 illustrates the inserting of the Z-shaped boneplate into the slot.

FIG. 5 Remove the pliers, raise up the fractured end with the longer slot a little, insert the whole plate into the boneslot 28a.

Figure 6:
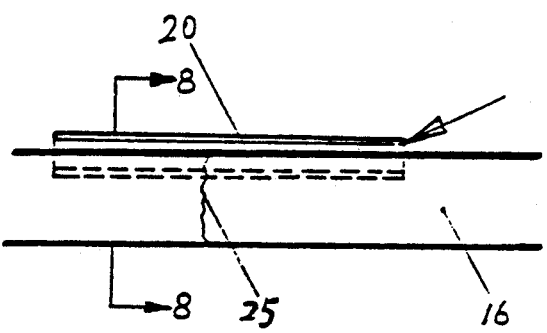
FIG. 6 shows the reduction of the fractured ends and that the Z-shaped boneplate spans the two sides of the fractured ends.

FIG. 6 Align the fractured ends of the bone again and beat the plate into the opposite slot 28b and make the midpoint coincide with the fractured section. In this way, the Z-shaped boneplate spans the two sides of the fractured bone and fixes the fractured ends firmly.

Figure 7:
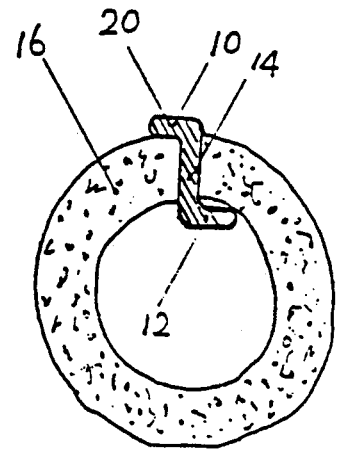
FIG. 7 is the bone cross section of inserting a Z-shaped boneplate into the boneslot.

FIG. 7 shows the cross section 8—8 of FIG. 6 that a Z-shaped boneplate inserted into the boneslot of the fractured ends. In the drawing, the web member 14 is inserted into the boneslot, the upper flange member 10 locks the outer surface of the bone cortex on both sides of the fracture, and the lower of flange member 12 locks the inner surface of the bone marrow cavity on both sides of the fracture.

Figure 8:
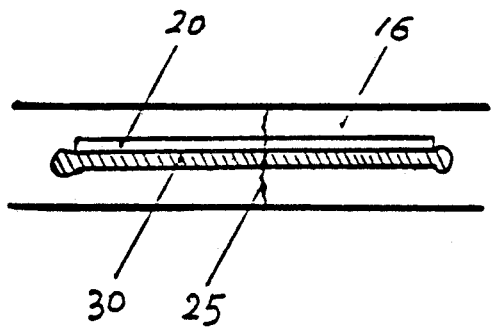
FIG. 8 shows the method for rejecting the Z-shaped boneplate from the plated bone.

FIG. 8 shows the method for rejecting of boneplate after the fracture is healed, you may chisel the original boneslot a bit wider to reject the plate. If the fractured bone is not yet healed, you may reject the plate in an opposite way against the order hereinbefore.

The Construction and Size of the Present Invention

As showed in FIG. 1, a Z-shaped boneplate is made up of a web 14, an upper flange member 10 and a lower flange member 12 which is paralleled to the upper flange. There are two types of Z-shaped boneplates: one with a tail flange member (FIG. 1b) and one without a tail flange member (FIG. 1a). Longitudinally it is an elongated Z-shaped cross section beam and a boneplate without a tail flange, a Z-shaped uniform beam. The size of the plate depends on seven parameters which very according to the thickness of the bone cortex at the fractured section where the plate is to be inserted. Suppose the thickness $t=1$ (see FIG. 2), the seven parameters are then as follows (see FIG. 1):

| | |
|---|---|
| The length of the Z-shaped boneplate | $L = 5-15$ |
| The thickness of the Z-shaped boneplate | $T = 1/15-1/5$ |
| The height of the web member | $H = 1-1.5$ |
| The breadth of the flange member | $B = 1/5-1$ |
| The angle flanged by a flange member and the web member | $\phi = 60°-120°$ |

FIG. 1b shows a tail flange member 15 extends from the lower flange member 12. The tail flange member is used to enlarge the contact area between the Z-shaped boneplate and the internal contour of a hollow bone and hence increases the supporting area of the conduction of the bone stress. The tail flange member extends downwards from the two outer ends of the lower flange member towards the middle part along the surface of the bone marrow cavity (see FIG. 2d). Its size depends on the tail flange angle $\alpha$ and its width l. The tail flange angle ranges between 120° and 180°. The width of tail flange member ranges between O and L. In the case that there is no tail flange member (see FIG. 1a), $\alpha=180°$, $l=0$. In the case of a full tail flange $\alpha=0°$, $l=L$.

Therefore, according to the different thickness of the bone cortex t and the seven parameters mentioned above, a set of Z-shaped boneplates with different sizes and shapes can be designed to be chosen to use for operation. Besides, holes can be opened in the web member (see FIG. 1b,13). The holes can be round, elliptic, square or cancellate. The number of holes and their size and shape should be decided according to the principle that they do not affect the stability for fixation of the plate. By opening holes in the web member, the bone tissue can heal passing through the holes which speeds up the recovery of the fracture, and reinforce the fixation. Meanwhile, the plate is lightened and thus minimize the stimulation from foreign body caused by the remaining of the Z-shaped boneplate.

The Method For Operation

Prepare for the operation according to routine orthopedic prior-operation preparation. Perform the operation under aseptic condition. Preferably cut the incision in the outer part of the limb. Cut the skin, separate the tissue, strip the periosteum, expose and reduce the fractured ends. Mark a line as the bone slot on the surface of the bone, fix the fractured ends and cut a slot with its width the same as the thickness of the boneplate and with its longer side the same as length of the plate while the other side half the length. Raise up the end with the longer slot, insert the whole plate into the slot, reduce and align the fractured ends again, beat the inserted plate into the shorter boneslot until half of the plate is in the shorter slot. In this way, the fractured ends are fixed firmly. Then, suture the tissue and skin layer by layer.

Applied Field of the Present Invention

The present invention relates to internal fixation plate for fixation of long bone fracture and allograft materials in humans and mammals. The indications for Z-shaped boneplate operation are as follows: fracture of long bone in transverse, short-oblique, short spiral, nonunion and abnormal healing, etc. If used for child, there will be no arrest for bone growth. It is also suitable for fracture of non-tubular long bone such as clavicle fracture.

The Advantages of the Present Invention

1. The bending strength is greatly increased. Applying to mechanics principle, when a flat plate is curved to Z-shape in its cross section, its bending strength is greatly increased. Therefore, even if the Z-shape plate is very small and thin (compared with flat screw plate and compression plate), when inserted into the boneslot, it can still lock the two fracture ends firmly.

2. The fixation is stable and reliable. Inserting the web member into the boneslot ensures the reduction and alignment of the fractured ends. The upper and lower flanges lock the bone fracture and surface of the intramedullary cavity on both sides of the boneslot and thus avoid bending, torsion or any relative displacement between the fractured ends and make the fixation firm and reliable.

3. The axial physiological compression stress and minute strain between the fractured ends are preserved, which is in accordance with the principle of bone growth. The Z-shaped plate, being inserted into the boneslot, can slide a little longitudinally and makes the longitudinal movement of the fractured ends possible, results the fractured sections press to each other with no space in between. Certain elasticity in the Z-shaped plate itself enables the fractured ends to be under minute strain which help the healing. A Z-plated bone would not cause bone atrophy and refracture because there is no such blindness of increasing the compression when a compression plate is used, it does not cause arrest for bone growth for children because no screws are used.

4. The fixation causes no stress concentration. The load that fractured ends bear is well-distributed over the whole boneplate on its web member, upper and lower flanges and hence stress concentration is avoided. There will be no increasing of the bone absorption which leads to loosing of the fixation and stress destruction.

5. The operative wound is small: the small Z-shaped plate enables a small area of the stripping of the periosteum, minimized damage to the marrow cavity and to the blood supply. All these are beneficial to the healing of the bone.

6. No extra postoperation external fixation is required because of the stable and reliable fixation. Even if it is used for femur fracture, there is no need of fixation with plaster for a long period. Therefore, unfavorable results such as stiffness of the joints atrophy of the tissue and disturbance of circulation, etc., would not happen. There is no requirement for long time exercise for the functional recovery and the healing period is shortened.

7. A Z-shaped plate is small. Only a narrow upper flange (the area of an upper flange for femur fracture is about 2 cm$^2$) is exposed on the bone surface so the periosteum stripped is small. The exposed flange will soon be completely buried in the cortical bone and separated from the periosteum and would not cause pain. The boneplate is never to be removed from the bone.

8. Operative devices and technique are simplified. Only a set of Z-shaped plate and a suitable saw for the bone slot are needed for the operation. Also, Z-shaped plates are simple, small, easy to produce and the expense is low.

What is claimed is:

1. A boneplate for fixation of long bone fractures and allograft materials in humans and mammals comprising: an upper flange member, a lower flange member and a web member connecting the upper and lower flange members, the upper flange member and lower flange member each extending from opposite ends of the web and in opposite directions transverse to the web member to form a boneplate which is Z-shaped in cross section.

2. The boneplate as defined in claim 1, wherein the upper and lower flanges are parallel to each other.

3. The boneplate as defined in claim 1, wherein the upper and lower flanges extend from the web member at a right angle.

4. The boneplate as defined in claim 1, wherein a tail flange member extends form the lower flane member and is shaped to conform to the internal contour of a hollow bone together with the lower flange member.

5. The boneplate as defined in claim 1, wherein the web member contains at least one aperture.

6. A method of inserting a Z-shaped boneplate in a boneslot for internal fixation of long bone fractures, the method comprising the steps of:
   a) providing a Z-shaped boneplate as defined in claim 1;
   b) exposing and reducing the bone at the are of the fracture;
   c) cutting a slot in the bone transverse to and spanning two fracture ends of the bone;
   d) inserting the web member and the Z-shaped boneplate provided in step (a) in the slot made in one fracture segment of the bone;
   e) approximating two fractured ends so as to align the bone and slot;
   f) driving the Z-shaped boneplate along the slot and across the area of the fracture so that the Z-shaped boneplate spans and fixes the two sides of the fractured bone with the boneplate contained in each fracture segment of the bone.

7. The method of claim wherein step (c) further comprises the steps of:
   a) clamping the two fractured ends of the bone in aligned and reduced condition;
   b) scoring a substantially straight line spanning the fracture longitudinally along the bone surface with the length of the portion f the line on one side of the fracture being at least equal to the length of the boneplate and the length of the portion of the line on the other side of the fracture being approximately half the length of the boneplate;
   c) cutting a slot in the bone along the line scored on the bone, the width of the slot being equal to the thickness (T) of the Z-shaped boneplate.

* * * * *